US011073513B2

(12) United States Patent
Dryga et al.

(10) Patent No.: US 11,073,513 B2
(45) Date of Patent: *Jul. 27, 2021

(54) SEPARATING TARGET ANALYTES USING ALTERNATING MAGNETIC FIELDS

(71) Applicant: DNAE Group Holdings Limited, London (GB)

(72) Inventors: Sergey A. Dryga, Albuquerque, NM (US); Victor C. Esch, Albuquerque, NM (US); Richard G. Saul, Gaithersburg, MD (US); Andrew F. McDowell, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 512 days.

This patent is subject to a terminal disclaimer.

(21) Appl. No.: 15/206,751

(22) Filed: Jul. 11, 2016

(65) Prior Publication Data

US 2016/0327550 A1    Nov. 10, 2016

Related U.S. Application Data

(63) Continuation of application No. 12/855,147, filed on Aug. 12, 2010, now Pat. No. 9,389,225.

(Continued)

(51) Int. Cl.
*G01N 33/543* (2006.01)
*G01N 33/569* (2006.01)
(Continued)

(52) U.S. Cl.
CPC . *G01N 33/54326* (2013.01); *G01N 33/54333* (2013.01); *G01N 33/56911* (2013.01);
(Continued)

(58) Field of Classification Search
CPC ....... G01N 33/56911; G01N 33/54326; G01N 33/54333; G01N 33/5434; G01N 2446/00–2446/90; G01N 27/745
(Continued)

(56) References Cited

U.S. PATENT DOCUMENTS 3,970,518 A    7/1976  Giaever
4,018,886 A    4/1977  Giaever
(Continued)

FOREIGN PATENT DOCUMENTS

CA    2 342 047 A1    9/2001
EP    2138835 a1      12/2009
(Continued)

OTHER PUBLICATIONS

Beyor et al. "Integrated Capture, Concentration, Polymerase Chain Reaction, and Capillary Electrophoretic Analysis of Pathogens on a Chip" Anal Chem. May 1, 2009 ;81(9):3523-8. doi: 10.1021/ac900060r, Published on Web Apr. 2, 2009.*
(Continued)

*Primary Examiner* — Christine Foster
(74) *Attorney, Agent, or Firm* — Brown Rudnick LLP; Thomas C. Meyers

(57) ABSTRACT

The invention generally relates to using magnetic particles and alternating magnet fields to separate a target analyte from a sample. In certain embodiments, methods of the invention involve contacting a sample with magnetic particles including first moieties specific for a target analyte, thereby forming target/particle complexes in the sample, flowing the sample through a channel including second moieties attached to at least one surface of the channel, applying alternating magnetic fields to the flowing sample to result in target/particle complexes being brought into proximity of the surface to bind the second moieties and unbound
(Continued)

particles remaining free in the sample, binding the target/particle complexes to the second moieties, and washing away unbound particles and unbound analytes of the sample.

7 Claims, 3 Drawing Sheets

Related U.S. Application Data

(60) Provisional application No. 61/326,588, filed on Apr. 21, 2010.

(51) Int. Cl.
    *C07K 16/12*     (2006.01)
    *C12Q 1/689*     (2018.01)

(52) U.S. Cl.
    CPC . *B01L 2200/0647* (2013.01); *B01L 2400/043* (2013.01); *C07K 16/1267* (2013.01); *C12Q 1/689* (2013.01); *G01N 2333/195* (2013.01); *G01N 2446/20* (2013.01)

(58) Field of Classification Search
    USPC ........................................................ 436/526
    See application file for complete search history.

(56) References Cited

U.S. PATENT DOCUMENTS

| | | | |
|---|---|---|---|
| 4,180,563 A | 12/1979 | Fauve | |
| 4,230,685 A | 10/1980 | Senyei et al. | |
| 4,267,234 A | 5/1981 | Rembaum | |
| 4,434,237 A | 2/1984 | Dinarello | |
| 4,452,773 A | 6/1984 | Molday | |
| 4,551,435 A | 11/1985 | Liberti et al. | |
| 4,554,088 A | 11/1985 | Whitehead et al. | |
| 4,659,678 A | 4/1987 | Forrest et al. | |
| 4,677,055 A | 6/1987 | Dodin et al. | |
| 4,683,195 A | 7/1987 | Mullis et al. | |
| 4,683,202 A | 7/1987 | Mullis | |
| 4,695,393 A | 9/1987 | Chagnon et al. | |
| 4,795,698 A | 1/1989 | Owen et al. | |
| 4,851,330 A | 7/1989 | Kohne | |
| 4,901,018 A | 2/1990 | Lew | |
| 4,925,788 A | 5/1990 | Liberti | |
| 4,942,124 A | 7/1990 | Church | |
| 4,988,617 A | 1/1991 | Landegren et al. | |
| 5,004,699 A | 4/1991 | Winters | |
| 5,047,321 A | 9/1991 | Loken et al. | |
| 5,057,413 A | 10/1991 | Terstappen et al. | |
| 5,089,386 A | 2/1992 | Stackebrandt et al. | |
| 5,108,933 A | 4/1992 | Liberti et al. | |
| 5,136,095 A | 8/1992 | Tarnowski et al. | |
| 5,149,625 A | 9/1992 | Church et al. | |
| 5,164,297 A | 11/1992 | Josephson et al. | |
| 5,186,827 A | 2/1993 | Liberti et al. | |
| 5,200,084 A | 4/1993 | Liberti et al. | |
| 5,229,724 A | 7/1993 | Zeiger | |
| 5,234,816 A | 8/1993 | Terstappen | |
| 5,242,794 A | 9/1993 | Whiteley et al. | |
| 5,254,460 A | 10/1993 | Josephson et al. | |
| 5,270,163 A | 12/1993 | Gold et al. | |
| 5,338,687 A | 8/1994 | Lee et al. | |
| 5,342,790 A | 8/1994 | Levine et al. | |
| 5,460,979 A | 10/1995 | Levine et al. | |
| 5,466,574 A | 11/1995 | Liberti et al. | |
| 5,494,810 A | 2/1996 | Barany et al. | |
| 5,512,332 A | 4/1996 | Liberti et al. | |
| 5,541,072 A | 7/1996 | Wang et al. | |
| 5,583,024 A | 12/1996 | McElroy et al. | |
| 5,583,033 A | 12/1996 | Terstappen et al. | |
| 5,597,531 A | 1/1997 | Liberti et al. | |
| 5,604,097 A | 2/1997 | Brenner | |
| 5,605,805 A | 2/1997 | Verwer et al. | |
| 5,622,831 A | 4/1997 | Liberti et al. | |
| 5,622,853 A | 4/1997 | Terstappen et al. | |
| 5,636,400 A | 6/1997 | Young | |
| 5,646,001 A | 7/1997 | Terstappen et al. | |
| 5,654,636 A | 8/1997 | Sweedler et al. | |
| 5,660,990 A | 8/1997 | Rao et al. | |
| 5,674,713 A | 10/1997 | McElroy et al. | |
| 5,677,133 A | 10/1997 | Oberhardt | |
| 5,681,478 A | 10/1997 | Lea et al. | |
| 5,684,401 A | 11/1997 | Peck et al. | |
| 5,695,934 A | 12/1997 | Brenner | |
| 5,695,946 A | 12/1997 | Benjamin et al. | |
| 5,698,271 A | 12/1997 | Liberti et al. | |
| 5,700,673 A | 12/1997 | McElroy et al. | |
| 5,741,714 A | 4/1998 | Liberti | |
| 5,768,089 A | 6/1998 | Finnigan | |
| 5,770,461 A | 6/1998 | Sakazume et al. | |
| 5,773,307 A | 6/1998 | Colin et al. | |
| 5,776,710 A | 7/1998 | Levine et al. | |
| 5,795,470 A | 8/1998 | Wang et al. | |
| 5,821,066 A | 10/1998 | Pyle et al. | |
| 5,834,217 A | 11/1998 | Levine et al. | |
| 5,840,580 A | 11/1998 | Terstappen et al. | |
| 5,846,719 A | 12/1998 | Brenner et al. | |
| 5,863,722 A | 1/1999 | Brenner | |
| 5,866,099 A | 2/1999 | Owen et al. | |
| 5,869,252 A | 2/1999 | Bouma et al. | |
| 5,876,593 A | 3/1999 | Liberti et al. | |
| 5,925,573 A | 7/1999 | Colin et al. | |
| 5,935,825 A | 8/1999 | Nishimura et al. | |
| 5,948,412 A | 9/1999 | Murphy | |
| 5,955,583 A | 9/1999 | Beavo et al. | |
| 5,985,153 A | 11/1999 | Dolan et al. | |
| 5,993,665 A | 11/1999 | Terstappen et al. | |
| 6,013,188 A | 1/2000 | Terstappen et al. | |
| 6,013,532 A | 1/2000 | Liberti et al. | |
| 6,060,882 A | 5/2000 | Doty | |
| 6,097,188 A | 8/2000 | Sweedler et al. | |
| 6,100,099 A | 8/2000 | Gordon et al. | |
| 6,120,856 A | 9/2000 | Liberti et al. | |
| 6,136,182 A | 10/2000 | Dolan et al. | |
| 6,138,077 A | 10/2000 | Brenner | |
| 6,146,838 A | 11/2000 | Williams et al. | |
| 6,150,516 A | 11/2000 | Brenner et al. | |
| 6,172,214 B1 | 1/2001 | Brenner | |
| 6,172,218 B1 | 1/2001 | Brenner | |
| 6,194,900 B1 | 2/2001 | Freeman et al. | |
| 6,228,624 B1 | 5/2001 | Terstappen | |
| 6,235,475 B1 | 5/2001 | Brenner et al. | |
| 6,236,205 B1 | 5/2001 | Ludeke et al. | |
| 6,242,915 B1 | 6/2001 | Hurd | |
| 6,265,150 B1 | 7/2001 | Terstappen et al. | |
| 6,287,791 B1 | 9/2001 | Terstappen et al. | |
| 6,307,372 B1 | 10/2001 | Sugarman et al. | |
| 6,326,787 B1 | 12/2001 | Cowgill | |
| 6,348,318 B1 | 2/2002 | Valkirs | |
| 6,352,828 B1 | 3/2002 | Brenner | |
| 6,361,749 B1 | 3/2002 | Terstappen et al. | |
| 6,361,944 B1 | 3/2002 | Mirkin et al. | |
| 6,365,362 B1 | 4/2002 | Terstappen et al. | |
| 6,395,879 B1 * | 5/2002 | Mandrell | C07K 16/121 424/164.1 |
| 6,397,094 B1 | 5/2002 | Ludeke et al. | |
| 6,404,193 B1 | 6/2002 | Dourdeville | |
| 6,456,072 B1 | 9/2002 | Webb et al. | |
| 6,469,636 B1 | 10/2002 | Baird et al. | |
| 6,487,437 B1 | 11/2002 | Viswanathan et al. | |
| 6,495,357 B1 | 12/2002 | Fuglsang et al. | |
| 6,512,941 B1 | 1/2003 | Weiss et al. | |
| 6,514,415 B2 | 2/2003 | Hatch et al. | |
| 6,551,843 B1 | 4/2003 | Rao et al. | |
| 6,555,324 B1 | 4/2003 | Olweus et al. | |
| 6,582,938 B1 | 6/2003 | Su et al. | |
| 6,587,706 B1 | 7/2003 | Viswanathan | |
| 6,594,517 B1 | 7/2003 | Nevo | |
| 6,620,627 B1 | 9/2003 | Liberti et al. | |
| 6,623,982 B1 | 9/2003 | Liberti et al. | |
| 6,623,983 B1 | 9/2003 | Terstappen et al. | |
| 6,645,731 B2 | 11/2003 | Terstappen et al. | |

(56) References Cited

U.S. PATENT DOCUMENTS

| | | |
|---|---|---|
| 6,660,159 B1 | 12/2003 | Terstappen et al. |
| 6,696,838 B2 | 2/2004 | Raftery et al. |
| 6,700,379 B2 | 3/2004 | Peck et al. |
| 6,788,061 B1 | 9/2004 | Sweedler et al. |
| 6,790,366 B2 | 9/2004 | Terstappen et al. |
| 6,818,395 B1 | 11/2004 | Quake et al. |
| 6,822,454 B2 | 11/2004 | Peck et al. |
| 6,845,262 B2 | 1/2005 | Albert et al. |
| 6,858,384 B2 | 2/2005 | Terstappen et al. |
| 6,867,021 B2 | 3/2005 | Maes et al. |
| 6,876,200 B2 | 4/2005 | Anderson et al. |
| 6,890,426 B2 | 5/2005 | Terstappen et al. |
| 6,898,430 B1 | 5/2005 | Liberti et al. |
| 6,914,538 B2 | 7/2005 | Baird et al. |
| 6,958,609 B2 | 10/2005 | Raftery et al. |
| 7,011,794 B2 | 3/2006 | Kagan et al. |
| 7,056,657 B2 | 6/2006 | Terstappen et al. |
| 7,078,224 B1 | 7/2006 | Bitner et al. |
| 7,096,057 B2 | 8/2006 | Rockett et al. |
| 7,141,978 B2 | 11/2006 | Peck et al. |
| 7,169,560 B2 | 1/2007 | Lapidus et al. |
| 7,200,430 B2 | 4/2007 | Thomas et al. |
| 7,202,667 B2 | 4/2007 | Barbic |
| RE39,793 E | 8/2007 | Brenner |
| 7,271,592 B1 | 9/2007 | Gerald, II et al. |
| 7,274,191 B2 | 9/2007 | Park et al. |
| 7,282,180 B2 | 10/2007 | Tibbe et al. |
| 7,282,337 B1 | 10/2007 | Harris |
| 7,282,350 B2 | 10/2007 | Rao et al. |
| 7,304,478 B2 | 12/2007 | Tsuda et al. |
| 7,332,288 B2 | 2/2008 | Terstappen et al. |
| 7,345,479 B2 | 3/2008 | Park et al. |
| 7,393,665 B2 | 7/2008 | Brenner |
| 7,403,008 B2 | 7/2008 | Blank et al. |
| 7,405,567 B2 | 7/2008 | McDowell |
| 7,523,385 B2 | 4/2009 | Nguyen et al. |
| 7,537,897 B2 | 5/2009 | Brenner et al. |
| 7,544,473 B2 | 6/2009 | Brenner |
| 7,564,245 B2 | 7/2009 | Lee |
| 7,666,308 B2 | 2/2010 | Scholtens et al. |
| 7,688,777 B2 | 3/2010 | Liberti, Jr. et al. |
| 7,764,821 B2 | 7/2010 | Coumans et al. |
| 7,815,863 B2 | 10/2010 | Kagan et al. |
| 7,820,454 B2 * | 10/2010 | Su ............... B01F 11/0266 436/526 |
| 7,828,968 B2 | 11/2010 | Tibbe et al. |
| 7,863,012 B2 | 1/2011 | Rao et al. |
| 7,901,950 B2 | 3/2011 | Connelly et al. |
| 7,943,397 B2 | 5/2011 | Tibbe et al. |
| 8,067,938 B2 | 11/2011 | McDowell |
| 8,102,176 B2 | 1/2012 | Lee |
| 8,110,101 B2 | 2/2012 | Tibbe et al. |
| 8,111,669 B2 | 2/2012 | Liberti, Jr. et al. |
| 8,128,890 B2 | 3/2012 | Droog et al. |
| 8,841,104 B2 * | 9/2014 | Dryga ............... C07K 1/22 435/173.9 |
| 8,889,368 B2 | 11/2014 | Barbreau et al. |
| 9,389,225 B2 * | 7/2016 | Dryga ............... C07K 1/22 |
| 9,428,547 B2 | 8/2016 | Dryga et al. |
| 9,434,940 B2 | 9/2016 | Dykes |
| 9,476,812 B2 | 10/2016 | Dryga et al. |
| 9,551,704 B2 | 1/2017 | Norvell |
| 9,562,896 B2 * | 2/2017 | Esch ............... C07K 1/22 |
| 9,599,610 B2 | 3/2017 | Sitdikov et al. |
| 9,671,395 B2 * | 6/2017 | Dryga ............... C07K 1/22 |
| 9,696,302 B2 * | 7/2017 | Dryga ............... C07K 1/22 |
| 9,869,671 B2 * | 1/2018 | Dryga ............... C07K 1/22 |
| 2001/0018192 A1 | 8/2001 | Terstappen et al. |
| 2002/0009759 A1 | 1/2002 | Terstappen et al. |
| 2002/0012669 A1 | 1/2002 | Presnell et al. |
| 2002/0098531 A1 | 7/2002 | Thacker |
| 2002/0130661 A1 | 9/2002 | Raftery et al. |
| 2002/0132228 A1 | 9/2002 | Terstappen et al. |
| 2002/0141913 A1 | 10/2002 | Terstappen et al. |
| 2002/0164629 A1 | 11/2002 | Quake et al. |
| 2002/0164659 A1 | 11/2002 | Rao et al. |
| 2002/0172987 A1 | 11/2002 | Terstappen et al. |
| 2003/0003441 A1 | 1/2003 | Colston et al. |
| 2003/0022231 A1 | 1/2003 | Wangh et al. |
| 2003/0054376 A1 | 3/2003 | Mullis et al. |
| 2003/0088181 A1 | 5/2003 | Gleich |
| 2003/0092029 A1 | 5/2003 | Josephson et al. |
| 2003/0129676 A1 | 7/2003 | Terstappen et al. |
| 2003/0203507 A1 | 10/2003 | Liberti et al. |
| 2003/0206577 A1 | 11/2003 | Liberti et al. |
| 2003/0222648 A1 | 12/2003 | Fan |
| 2004/0004043 A1 | 1/2004 | Terstappen et al. |
| 2004/0018611 A1 | 1/2004 | Ward et al. |
| 2004/0072269 A1 | 4/2004 | Rao et al. |
| 2004/0076990 A1 | 4/2004 | Picard et al. |
| 2004/0087032 A1 | 5/2004 | Chandler et al. |
| 2004/0101443 A1 | 5/2004 | Kagan et al. |
| 2004/0118757 A1 | 6/2004 | Terstappen et al. |
| 2004/0151629 A1 | 8/2004 | Pease et al. |
| 2005/0003464 A1 | 1/2005 | Tibbe et al. |
| 2005/0006990 A1 | 1/2005 | Williquette et al. |
| 2005/0026144 A1 | 2/2005 | Maes et al. |
| 2005/0043521 A1 | 2/2005 | Terstappen et al. |
| 2005/0069900 A1 | 3/2005 | Lentrichia |
| 2005/0079520 A1 | 4/2005 | Wu |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0245814 A1 | 11/2005 | Anderson et al. |
| 2006/0024756 A1 | 2/2006 | Tibbe et al. |
| 2006/0115380 A1 | 6/2006 | Kagan et al. |
| 2006/0129237 A1 | 6/2006 | Imran |
| 2006/0129327 A1 | 6/2006 | Kim et al. |
| 2006/0147901 A1 | 7/2006 | Jan et al. |
| 2006/0194192 A1 | 8/2006 | Rao et al. |
| 2006/0233712 A1 | 10/2006 | Penades et al. |
| 2006/0257847 A1 | 11/2006 | Scholtens et al. |
| 2006/0257945 A1 | 11/2006 | Masters et al. |
| 2006/0281094 A1 | 12/2006 | Squirrell et al. |
| 2007/0037173 A1 | 2/2007 | Allard et al. |
| 2007/0037231 A1 | 2/2007 | Sauer-Budge et al. |
| 2007/0090836 A1 | 4/2007 | Xiang et al. |
| 2007/0114181 A1 | 5/2007 | Li et al. |
| 2007/0116602 A1 | 5/2007 | Lee |
| 2007/0117158 A1 | 5/2007 | Coumans et al. |
| 2007/0152669 A1 | 7/2007 | Park et al. |
| 2007/0152670 A1 | 7/2007 | Park et al. |
| 2007/0154960 A1 | 7/2007 | Connelly et al. |
| 2007/0166835 A1 | 7/2007 | Bobrow et al. |
| 2007/0183935 A1 | 8/2007 | Clemmens et al. |
| 2007/0231926 A1 | 10/2007 | Ikeda |
| 2007/0264629 A1 | 11/2007 | Holmes et al. |
| 2007/0296413 A1 | 12/2007 | Park et al. |
| 2008/0026451 A1 | 1/2008 | Braman et al. |
| 2008/0042650 A1 | 2/2008 | McDowell |
| 2008/0081330 A1 | 4/2008 | Kahvejian |
| 2008/0099715 A1 | 5/2008 | Adams et al. |
| 2008/0113350 A1 | 5/2008 | Terstappen |
| 2008/0135490 A1 | 6/2008 | Li et al. |
| 2008/0199851 A1 | 8/2008 | Egan et al. |
| 2008/0204011 A1 | 8/2008 | Shoji |
| 2008/0204022 A1 | 8/2008 | Sillerud et al. |
| 2008/0272788 A1 | 11/2008 | McDowell |
| 2008/0286838 A1 | 11/2008 | Yuan et al. |
| 2008/0315875 A1 | 12/2008 | Sillerud |
| 2009/0026082 A1 | 1/2009 | Rothberg et al. |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0127589 A1 | 5/2009 | Rothberg et al. |
| 2009/0134869 A1 | 5/2009 | Lee |
| 2009/0136946 A1 | 5/2009 | Connelly et al. |
| 2009/0146658 A1 | 6/2009 | McDowell et al. |
| 2009/0148847 A1 | 6/2009 | Kokoris et al. |
| 2009/0156572 A1 | 6/2009 | Ikeura et al. |
| 2009/0173681 A1 | 7/2009 | Siddiqi |
| 2009/0191535 A1 | 7/2009 | Connelly et al. |
| 2009/0227044 A1 | 9/2009 | Dosev et al. |

(56) References Cited

U.S. PATENT DOCUMENTS

| | | |
|---|---|---|
| 2009/0246796 A1 | 10/2009 | Bernard et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0035252 A1 | 2/2010 | Rothberg et al. |
| 2010/0068723 A1 | 3/2010 | Jovanovich et al. |
| 2010/0072994 A1 | 3/2010 | Lee et al. |
| 2010/0129785 A1 | 5/2010 | Pris et al. |
| 2010/0137143 A1 | 6/2010 | Rothberg et al. |
| 2010/0144005 A1 | 6/2010 | Bin Kingombe et al. |
| 2010/0184033 A1 | 7/2010 | West et al. |
| 2010/0188073 A1 | 7/2010 | Rothberg et al. |
| 2010/0197507 A1 | 8/2010 | Rothberg et al. |
| 2010/0219824 A1 | 9/2010 | Sillerud et al. |
| 2010/0225315 A1 | 9/2010 | McDowell |
| 2010/0282617 A1 | 11/2010 | Rothberg et al. |
| 2010/0282788 A1 | 11/2010 | Liberti |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0086338 A1 | 4/2011 | Hwang et al. |
| 2011/0091987 A1 | 4/2011 | Weissleder et al. |
| 2011/0098623 A1 | 4/2011 | Zhang et al. |
| 2011/0104718 A1 | 5/2011 | Rao et al. |
| 2011/0137018 A1 | 6/2011 | Chang-Yen et al. |
| 2011/0183398 A1 | 7/2011 | Dasaratha et al. |
| 2011/0262893 A1 | 10/2011 | Dryga et al. |
| 2011/0262925 A1 | 10/2011 | Dryga et al. |
| 2011/0262926 A1 | 10/2011 | Esch et al. |
| 2011/0262927 A1 | 10/2011 | Dryga et al. |
| 2011/0262932 A1 | 10/2011 | Esch et al. |
| 2011/0262933 A1 | 10/2011 | Dryga et al. |
| 2011/0262989 A1 | 10/2011 | Clarizia et al. |
| 2011/0263833 A1 | 10/2011 | Dryga et al. |
| 2011/0300551 A1 | 12/2011 | Rao et al. |
| 2011/0300609 A1 | 12/2011 | Lim et al. |
| 2011/0301042 A1 | 12/2011 | Steinmann et al. |
| 2012/0045828 A1 | 2/2012 | Davis et al. |
| 2012/0094275 A1 | 4/2012 | Rao et al. |
| 2012/0100546 A1 | 4/2012 | Lowery, Jr. et al. |
| 2012/0112744 A1 | 5/2012 | McDowell et al. |
| 2013/0109590 A1 | 5/2013 | Clarizia et al. |
| 2013/0196341 A1 | 8/2013 | Neely et al. |
| 2013/0203634 A1 | 8/2013 | Jovanovich et al. |
| 2013/0316355 A1 | 11/2013 | Dryga et al. |
| 2014/0100136 A1 | 4/2014 | Clarizia et al. |
| 2014/0170021 A1 | 6/2014 | Dryga |
| 2014/0170639 A1 | 6/2014 | Norvell |
| 2014/0170640 A1 | 6/2014 | Dykes |
| 2014/0170641 A1 | 6/2014 | Macemon |
| 2014/0170652 A1 | 6/2014 | Sitdikov et al. |
| 2014/0170667 A1 | 6/2014 | Dykes et al. |
| 2014/0170669 A1 | 6/2014 | Vandervest |
| 2014/0170727 A1 | 6/2014 | Dryga et al. |
| 2014/0171340 A1 | 6/2014 | Dykes et al. |
| 2015/0212079 A1 | 7/2015 | Dryga et al. |

FOREIGN PATENT DOCUMENTS

| | | | | |
|---|---|---|---|---|
| EP | 2261650 A2 | 12/2010 | | |
| WO | 1988/003957 A1 | 6/1988 | | |
| WO | 89/06699 A1 | 7/1989 | | |
| WO | 90/08841 A1 | 8/1990 | | |
| WO | 91/02811 A1 | 3/1991 | | |
| WO | 92/08805 A1 | 5/1992 | | |
| WO | 92/15883 A1 | 9/1992 | | |
| WO | 99/53320 A1 | 10/1999 | | |
| WO | 01/73460 A1 | 10/2001 | | |
| WO | 02/98364 A2 | 12/2002 | | |
| WO | 2005/026762 A1 | 3/2005 | | |
| WO | 2005106480 A1 | 11/2005 | | |
| WO | 2007/018601 A1 | 2/2007 | | |
| WO | WO-2007089564 A2 * | 8/2007 | ....... | G01N 33/54333 |
| WO | 2007/123345 A1 | 11/2007 | | |
| WO | 2007/135099 A1 | 11/2007 | | |
| WO | 2007123342 A1 | 11/2007 | | |
| WO | WO-2008020228 A1 * | 2/2008 | ....... | G01N 33/56994 |
| WO | 2008/119054 A1 | 10/2008 | | |
| WO | 2008/139419 A1 | 11/2008 | | |
| WO | 2009/048673 A2 | 4/2009 | | |
| WO | 2009072003 A2 | 6/2009 | | |
| WO | WO-2010044007 A2 * | 4/2010 | ............ | B03C 5/028 |
| WO | 2011/133630 A1 | 10/2011 | | |
| WO | 2011/133632 A1 | 10/2011 | | |
| WO | 2011/133759 A1 | 10/2011 | | |
| WO | 2011/133760 A1 | 10/2011 | | |

OTHER PUBLICATIONS

Sista et al., 2008, Heterogeneous Immunoassays Using Magnetic beads on a Digital Microfluidic Platform, Lab Chip 8(2):2188-2196.

Butter et al., 2002, Synthesis and properties of iron ferrofluids, J. Magn. Magn. Mater. 252:1-3.

Lu et al., 2007, Magnetic Nanoparticles: Synthesis, Protection, Functionalization, and Application, Angew. Chem. Int. Ed. 46:1222-1244.

Matar et al., 1990, Magnetic particles derived from iron nitride, IEEE Transactions on magnetics 26(1):60-62.

Cold Spring Harbor Protocols, Recipe for Dulbecco's phosphate-buffered saline (Dulbecco's PBS, 2009, retrieved from http://cshprotocols.cshlp.Org/content/2009/3/pdb_rec11725. full?text_only=true on Mar. 9, 2015, one page.

Cheng et al, 2012, Concentration and detection of bacteria in virtual environmental samples based on non-immunomagnetic separation and quantum dots by using a laboratory-made system, Proc. of SPIE:82310Y-1-82310Y-18.

Ohno et al, 2011, Effects of Blood Group Antigen-Binding Adhesin Expression during Helicobacter pylori Infection of Mongolian Gerbils, The Journal of Infectious Diseases 203:726-735.

Barany F. (1991) PNAS 88:189-193.

Narang et al., Methods Enzymol., 68:90 (1979).

Brown et al., Methods Enzymol., 68:109 (1979), "Chemical Synthesis and Cloning of a Tyrosine tRNA Gene".

Barany et al., Gene, 108:1 (1991).

Myers and Gelfand, Biochemistry 30:7661 (1991).

Levin, Cell 88:5-8 (1997).

Barany, F., Genome research, 1:5-16 (1991), "The Ligase Chain Reaction in a PCR World".

Margulies et al., Nature, 437: 376-380 (2005).

Olsvik et al. "Magnetic Separation Techniques in Diagnostic Microbiology" Clinical Microbiology Reviews (1994), pp. 43-54.

Chandler et al., Automated immunomagnetic separation and microarray detection of E. coli O157:H7 from poultry carcass rinse, Int. J. Food Micro., 70 (2001) 143-154.

Bruno et al., "Development of an Immunomagnetic Assay System for Rapid Detection of Bacteria and Leukocytes in Body Fluids," J Mol Recog, 9 (1996) 474-479.

Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.

Safarik et al., "The application of magnetic separations in applied Microbiology" Journal of Applied Bacteriology 1995, 78, 575-585.

Dam et al. "Garlic (Allium sativum) Lectins Bind to High Mannose Oligosaccharide Chains", Journal of Biological Chemistry vol. 273, No. 10, Issue of Mar. 6, pp. 5528-5535, 1998.

Fenwick et al., 1986, Mechanisms Involved in Protection Provided by Immunization against Core Lipopolysaccharides of *Escherichia*

(56) References Cited

OTHER PUBLICATIONS coli J5 from Lethal Haemophilus pleuropneumoniae Infections in Swine, Infection and Immunity 53(2):298-304.
Yu et al. "Development of a Magnetic Microplate Chemifluorimmunoassay for Rapid Detection of Bacteria and Toxin in Blood", Analytical Biochemistry 261 (1998), pp. 1-7.
The United States Naval Research Laboratory (NRL), "The FABS Device: Magnetic Particles", retrieved from http://www.nrl.navy.mil/chemistry/6170/6177/beads.php on Jan. 8, 2013, two pages.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Campuzano, et al., Bacterial Isolation by Lectin Modified Microengines, Nano Lett. Jan. 11, 2012; 12(1): 396-401.
Agrawal et al., 1990, Tetrahedron Letters 31:1543-46.
Harkins and Harrigan, "Labeling of Bacterial Pathogens for Flow Cytometric Detection and Enumeration" Curr Prot Cytom (2004) 11.17.1-11.17.20.
Takagi et al., Appl. Environ. Microbiol. 63:4504 (1997).
Cariello et al., Nucl Acids Res, 19:4193 (1991).
Lecomte et al. Nucl Acids Res. 11:7505 (1983).
Cann et al., Proc. Natl. Acad. Sci. 95:14250 (1998).
Braslaysky et al., PNAS, 100:3690-3694 (2003).
Moudrianakis et al., Proc. Natl. Acad. Sci. 53:564-71 (1965).
Vandeventer, J. Clin. Microbiol. Jul. 2011, 49(7):2533-39.
Carroll, N.M., E. E. Jaeger, et al. (2000). "Detection of and discrimination between grampositive and gram-negative bacteria in intraocular samples by using nested PCR." J Clin 15 Microbiol 38(5): 1753-1757.
Klaschik, S., L. E. Lehmann, et al. (2002). "Real-time PCR for detection and differentiation of gram-positive and gram-negative bacteria" J Clin Microbiol 40(11): 4304-4307.
Chien et al., J. Bacteriol, 127:1550 (1976).
Nordstrom et al., J. Biol. Chem. 256:3112 (1981).
Elnifro, Elfath M., et al. "Multiplex PCR: optimization and application in diagnostic virology." Clinical Microbiology Reviews 13.4 (2000): 559-570.
Soni et al., Clin Chem 53:1996-2001 (2007).
Diaz et al., Braz J. Med. Res., 31:1239 (1998).
Verma, Biochim Biophys Acta 473:1-38 (1977).
Harris et al., Science 320:106-109 (2008).
Dover, Jason E., et al. "Recent advances in peptide probe-based biosensors for detection of infectious agents." Journal of microbiological methods 781 (2009): 10-19.
Payne, M.J. et al., "The Use of Immobilized Lectins in the Separation of *Staphylococcus aureus*, *Escherichia coli*, *Listeria* and *Salmonella* spp. from Pure Cultures and Foods", Journal of Applied Bacteriology, 1992, No. 73, pp. 41-52 (12 Pages).
Extended European Search Report dated Feb. 2, 2017 for European Application No. 16190239.0 (8 Pages).
Furdui, Vasile I. et al., "Microfabricated Electrolysis Pump System for Isolating Rare Cells in Blood; Micro-Electrolysis Jumps for Blood", Journal of Micromechanics & Microengineering, vol. 13, No. 4, Jul. 1, 2003, pp. S164-S170 (7 Pages).
Furdui, Vasile I. et al., "Immunomagnetic T Cell Capture From Blood for PCR Analysis Using Microfluidic Systems", Lab on a Chip, 2004, vol. 4. No. 6, pp. 614-618 (5 Pages).
Yang et al., "Simultaneous Detection of *Escherichia coli* O157:H7 and *Salmonella typhimurium* Using Quantum Dots as Fluorescence Labels", Analyst 131(3), Mar. 2006, pp. 394-101 (8 Pages).
Wang Hong, Ph.D., "Rapid and Simultaneous Detection of Foodborne Bacterial Pathogens Using Multiplex Assays", Dissertation Abstract, University of Arkansas, 2010 (2 Pages).
NCBI Geo Gene Expression Omnibus, Entry for GSE22885, retrieved from https://www.nobi.nlm.nih.gov/geo/query/acc.cgi?aco=GSE22885 on May 25, 2017, with excerpts of files GPL10672_IMS_annotation.ann.txt.gz and GSM565264.txt.gz therein (five pages total), publicly available on Jul. 13, 2010 (5 Pages).

Gesbert et al. "Asparagine Assimilation is Critical for Intracellular Replication and Dissemination of Francisella" Cellular Microbiology, 2014, 16(3), pp. 434-449 (16 Pages).
Mulder, et al., Characterization of two human monoclonal antibodies reactive with HLA-B12 and HLA-B60, respectively, raised by in vitro secondary immunization of peripheral blood lymphocytes, Hum. Immunol., 36(3):186-192 (1993).
Nyquist, Thermal Agitation of Electrical Charge in Conductors, Phys. Rev., 32:110-113 (1928).
Margin, et al., High resolution microcoil 1H-NMR for mass-limited, nanoliter-volume samples, Science, 270:1967 (1995).
Olson, et al., High-resolution microcoil NMR for analysis of mass-limited, nanoliter samples, Anal. Chem., 70:645-650 (1998).
Pappas, et al., Cellular Separations: A Review of New Challenges in Analytical Chemistry, Analytica Chimica Acta, 601(1):26-35 (2007).
Peck, et al., Design and Analysis of Microcoils for NMR Microscopy, J. Magn. Reson. B 108:114-124 (1995).
Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qui, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Sealer, et al., Design and Testing of high sensitivity Microreceiver Coil Apparatus for Nuclear Magnetic Resonance and Imaging, Rev. Sci. Inst., 72:2171-2179 (2001).
Sealer, et al., Triaxial Magnetic Field Gradient System for Microcoil Magnetic Resonance Imaging, Rev. Sci. Inst., 71:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Skjerve, et al., Detection of Listeria monocytogenes in foods by immunomagnetic separation, Appl. Env. Microbiol., 56:3478 (1990).
Sorli, et al., Micro-spectrometer for NMR: analysis of small quantities in vitro, Meas. Sci. Technol., 15:877-880 (2004).
Stauber, et al., Rapid generation of monoclonal antibody-secreting hybridomas against African horse sickness virus by in vitro immunization and the fusion/cloning technique, J. Immunol. Methods, 161(2):157-168 (1993).
Stocker, et al., Nanoliter volume, high-resolution NMR Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Taktak, et al., Multiparameter Magnetic Relaxation Switch Assays, Analytical Chemistry, 79(23):8863-8869 (2007).
Torensama, et al., Monoclonal Antibodies Specific for the Phase-Variant O-Acetylated Ki Capsule of *Escerichia coli*, J. Clin. Microbiol., 29(7):1356-1358 (1991).
Trumbull, et al., Integrating microfabricated fluidic systems and NMR spectroscopy, IEEE Trans. Biomed. Eng., 47(1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Venkateswaran, et al., Production of Anti-Fibroblast Growth Factor Receptor Monoclonal Antibodies by In Vitro Immunization, Hybridoma, 11(6):729-739 (1992).
Vermunt, et al., Isolation of salmonelas by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Webb and Grant, Signal-to-Noise and Magnetic Susceptibility Tradeoffs in Solenoidal Microcoils for NMR, J. Magn. Reson. B, 113:83-87 (1996).

(56) References Cited

OTHER PUBLICATIONS

Wensink, et al., High Signal to Noise Ratio in Low-field NMR on a Chip: Simulations and Experimental Results, 17th IEEE MEMS, 407-410 (2004).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Zhao, et al., A rapid bioassay for single bacterial cell quantitation using bioconjugated nanoparticles, PNAS, 101(42):15027-15032 (2004).
Zordan, et al., Detection of Pathogenic E coli O157:H7 by a Hybrid Microfluidic SPR and Molecular Imaging Cytometry Device, Cytometry A, 75A:155-162 (2009).
Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.
Heijnen et al., 2009, Method for rapid detection of viable *Escherichia coli* in water using real-time NASBA, Water Research, 43:3124-3132.
Li et al., 2010, Chemiluminescent Detect of *E. coli* O157:H7 Using Immunological Method Based on Magnetic Nanoparticles, J. of Nanoscience and Nanotechnology 10:696-701.
Armenean, et al., Solenoidal and Planar Microcoils for NMR Spectroscopy, Proc. of the 25th Annual Int. Conf. of the IEEE Eng. in Med. and Bio. Soc., Cancun, Mexico, Sep. 17, 2003, pp. 3045-3048.
Behnia and Webb, Limited-Sample NMR Using Solenoidal Microcoils, Perfluorocarbon Plugs, and Capillary Spinning, Anal. Chem., 70:5326-5331 (1998).
Byrne, et al., Antibody-Based Sensors: Principles, Problems and Potential for Detection of Pathogens and Associated Toxins, Sensors, 9:4407-4445 (2009).
Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).
Ciobanu and Pennington, 3D Micron-scale MRI of Single Biological Cells, Solid State Nucl. Magn. Reson., 25:138-141 (2004).
Cross, et al., Choice of Bacteria in Animal Models of Sepsis, Infec. Immun. 61(7):2741-2747 (1983).
Djukovic, et al., Signal Enhancement in HPLC/Microcoil NMR Using Automated Column Trapping, Anal. Chem., 78:7154-7160 (2006).
Drancourt, et al., Diagnosis of Mediterranean Spotted Fever by Indirect Immunofluorescence of Rickettsia conorii in Circulating Endothelial Cells Isolated with Monoclonal Antibody-Coated Immunomagnetic Beads, J. Infectious Diseases, 166(3):660-663, 1992.
Fan, et al., Self-assembly of ordered, robust, three-dimensional gold nanocrystal/silica arrays, Science, 304:567 (2004).
Fu, et al., Rapid Detection of *Escherichia coli* O157:H7 by Immunogmagnetic Separation and Real-time PCR, Int. J. Food Microbiology, 99(1):47-57, (2005).
Goding, J.W., Conjugation of antibodies with fluorochromes: modifications to the standard methods, J. Immunol. Meth., 13:215 (1976).
Goloshevsky, et al., Development of Low Field Nuclear Magnetic Resonance Microcoils, Rev. Sci. Inst.., 76:024101-1 to 024101-6 (2005).
Goloshevsky, et al., Integration of Biaxial Planar Gradient Coils and an RF Microcoil for NMR Flow Imaging, Meas. Sci. Technol., 16:505-512 (2005).
Grant, et al., Analysis of Multilayer Radio Frequency Microcoils for Nuclear Magnetic Resonance Spectroscopy, IEEE Trans. Magn., 37:2989-2998 (2001).
Grant, et al., NMR Spectroscopy of Single Neurons, Magn. Reson. Med., 44:19-22 (2000).
Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Hijmans, et al., An immunofluorescence procedure for the detection of intracellular immunoglobulins, Clin. Exp. Immunol., 4:457 (1969).
Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Inai, et al., Immunohistochemical detection of an enamel protein-related epitope in rat bone at an early stage of osteogenesis, Histochemistry, 99(5):335-362 (1993).
Engvall, Enzyme immunoassay ELISA and EMIT, Meth. in Enzymol., 70:419-439 (1980).
ISR and Written Opinion in PCT/US2008/058518, dated Jul. 7, 2008, 21 pages.
ISR and Written Opinion in PCT/US2008/062473, dated Oct. 29, 2008, 20 pages.
ISR and Written Opinion in PCT/US2008/080983, dated Mar. 3, 2009, 14 pages.
ISR and Written Opinion in PCT/US2009/067577, dated Feb. 5, 2010, 13 pages.
International Search Report in PCT/US2011/33184, dated Jul. 25, 2011, 2 pages.
International Search Report in PCT/US2011/33186, dated Jun. 22, 2011, 1 page.
ISR and Written Opinion in PCT/US2011/48447, dated Dec. 22, 2011, 7 pages.
ISR and Written Opinion in PCT/US2011/48452, dated Dec. 22, 2011, 7 pages.
International Search Report in PCT/US2011/33411, dated Jun. 22, 2011, 1 page.
International Search Report in PCT/US2011/33410, dated Jul. 19, 2011, 2 pages.
Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Lee, et al., Chip-NRM Biosensor for detection and molecular analysis of cells, Nature Medicine, 14(8):869-874 (2008).
Lund, et al., Immunomagnetic separation and DNA hybridization for detection of enterotoxigenic *Escherichia coli* in a piglet model, J. Clin. Microbiol., 29:2259-2262 (1991).
Magin, et al., Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic NMR Probes, J. Magn. Reson., 164:242-255 (2003).
McDowell, et al., Operating Nanoliter Scale NMR Microcoils in a Itesla Field, J. Mag. Reson., 188(1):74-82 (2007).
Minard, et al., Solenoidal Microcoil Design, Part I: Optimizing RF Homogeneity and coil dimensions, Concepts in Magn Reson., 13(2):128-142 (2001).
Moresi and Magin, Miniature Permanent Magnet for Table-top NMR, Concept. Magn. Res., 19B:35-43 (2003).

\* cited by examiner

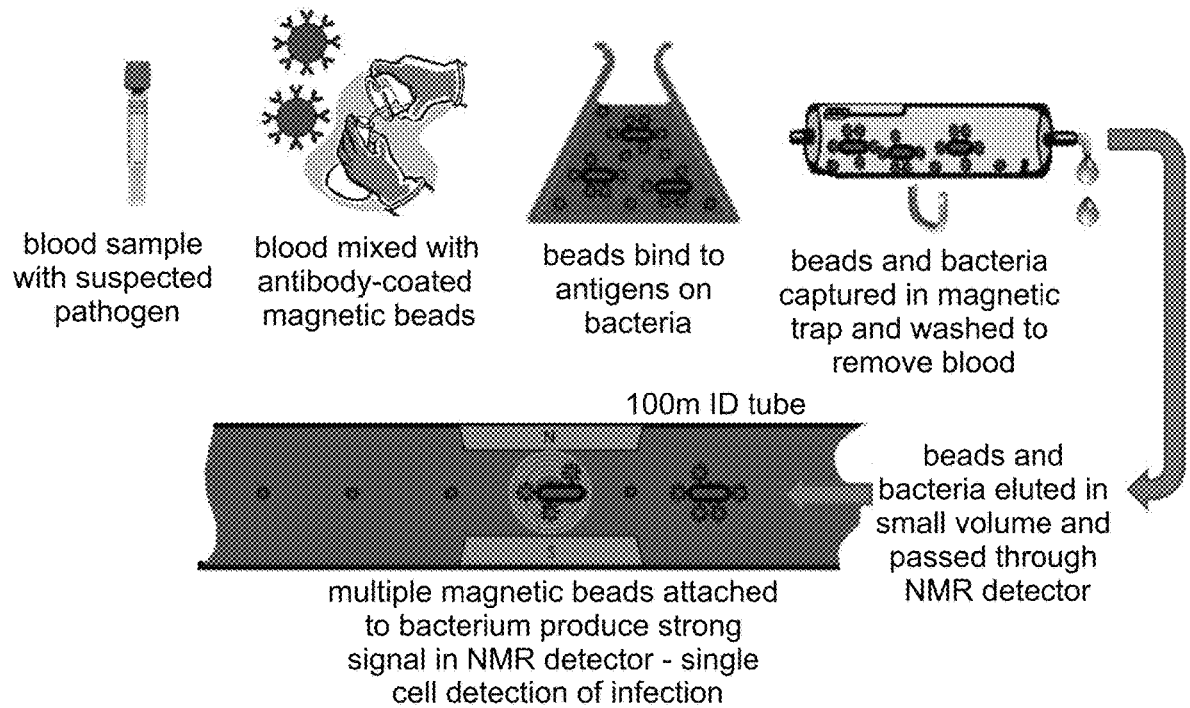
Figure 2 Panel A
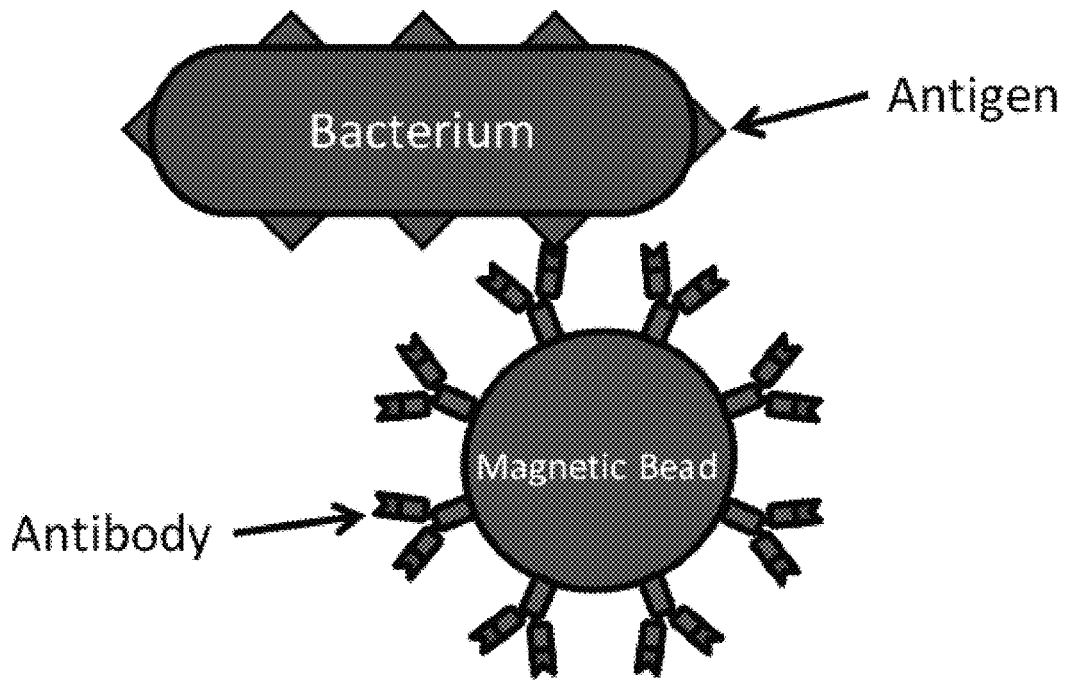
Figure 2 Panel B

SEPARATING TARGET ANALYTES USING ALTERNATING MAGNETIC FIELDS

RELATED APPLICATION

The present application is a continuation of U.S. patent application Ser. No. 12/855,147, filed Aug. 12, 2010 and recently allowed, which claims the benefit of and priority to U.S. provisional patent application Ser. No. 61/326,588, filed Apr. 21, 2010, the contents of each of which are incorporated by reference herein in their entirety.

FIELD OF THE INVENTION

The invention generally relates to using magnetic particles and alternating magnet fields to separate a target analyte from a sample.

BACKGROUND

Many laboratory and clinical procedures employ bio-specific affinity reactions. Such reactions are commonly utilized in diagnostic testing of biological samples, or for the separation of a wide range of target substances, especially biological entities such as cells, viruses, proteins, nucleic acids and the like. Various methods are available for analyzing or separating the above-mentioned target substances based upon complex formation between the substance of interest and another substance to which the target specifically binds. Separation of complexes from unbound material may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, Whitehead et al. (U.S. Pat. No. 4,554,088) and Hunter et al. (Immunoassays for Clinical Chemistry, pp. 147-162, eds., Churchill Livingston, Edinborough, 1983). Generally, any material that facilitates magnetic or gravitational separation may be employed for this purpose. More recently, the superiority of magnetics for performing such separations has led to its use in many applications.

A problem with magnetic separation protocols is that magnetic beads must be added in excess to a sample to ensure a sufficient amount of binding of beads to a target analyte in the sample, thus producing a sample that contains a very high percent of magnetic particles that are not bound to target analytes, as well as non-specific target entities. Non-specific target entities may for example be bound at a much lower efficiency, for example 1% of the surface area, while a target of interest might be loaded at 50% or nearly 100% of the available surface area or available antigenic cites. However, even 1% loading may be sufficient to impart force necessary for trapping in a magnetic gradient flow cell or sample chamber.

The presence of magnetic particles that are not bound to target analytes and non-specific target entities on the surface that includes the target/magnetic particle complexes interferes with the ability to successfully separate the target of interest of the remaining components of the mixture and unbound magnetic particles. The magnetic capture of the resulting mix, and close contact of magnetic particles with each other and labeled targets, result in the formation of aggregate that is hard to dispense and which might be resistant or inadequate for subsequent processing or analysis steps.

There is a need for methods for separating target analytes from a sample.

SUMMARY

The present invention generally relates to using magnetic particles having a target-specific binding moiety and alternating magnet fields to separate a target analyte from a sample. Methods of the invention allow for rapid (less than 1 hr) and efficient capture of target analytes from a sample while eliminating non-specific binding and reducing background noise resulting from excess magnetic particles not bound to target analytes. Methods of the invention involve contacting a sample with magnetic particles including first moieties specific for a target analyte, thereby forming target/particle complexes in the sample, flowing the sample through a channel including second moieties attached to at least one surface of the channel, applying alternating magnetic fields to the flowing sample to result in target/particle complexes being brought into proximity of the surface to bind the second moieties and unbound particles remaining free in the sample, binding the target/particle complexes to the second moieties, and washing away unbound particles and unbound analytes of the sample. A particular advantage of methods of the invention is for capture and isolation of bacteria and fungi directly from blood samples at low concentrations that are present in clinical samples (as low as 1 CFU/ml of bacteria in a blood sample).

In certain embodiments, the free magnetic particles and the target/particle complexes both interact numerous times with the surface of the flow channel. The targets are bound due to the specific interaction between the target analyte and the second moiety on the surface of the flow channel, and the free magnetic particles are not bound, and are thus continue flowing through the flow channel.

Methods of the invention may further involve eluting the bound target/particle complexes from the second moieties on the surface of the channel. Methods of the invention may further involve analyzing the eluted target/particle complexes. The target may be analyzed by a multitude of existing technologies, such as miniature NMR, Polymerase Chain Reaction (PCR), fluorescent labeling and visualization using microscopic observation, fluorescent in situ hybridization (FISH), growth-based antibiotic sensitivity tests, and variety of other methods that may be conducted with purified target without significant contamination from other sample components. In particular embodiments, analyzing involves flowing the target/particle complexes into an NMR instrument.

The target analyte refers to the target that will be captured and isolated by methods of the invention. The target may be a bacteria, a fungi, a protein, a nucleic acid, a receptor, a ligand, a cell, a virus, or any molecule known in the art. In a particular embodiment, the target is a bacteria.

Methods of the invention do not depend and are not limited by the type of sample. Any sample that includes a detectable target may be used with methods of the invention. The sample may be a biological sample (e.g., a human tissue or body fluid), an agricultural sample, or an environmental sample (e.g., a water or soil sample). In certain embodiments, the sample is a blood sample.

The first and second target-specific binding moieties will depend on the target to be captured. The moieties may be any capture moieties known in the art, such as an antibody, an aptamer, a phage, a nucleic acid, a protein, a receptor, or a ligand. In particular embodiments, the target-specific binding moieties are antibodies. In certain embodiments, the antibodies are specific for bacteria. In other embodiments, the antibodies are specific for fungi or viruses. In certain embodiments, the first and second moieties are the same. In alternative embodiments, the first and second moieties are different.

Generating alternating magnetic fields may be accomplished by any method known in the art. In certain embodiments, the alternating magnetic fields result from the channel being positioned between first and second sets of magnets, in which the channel remains stationary and the first and second sets of magnets are moved to alternate proximity to the channel, thereby producing the alternating magnetic fields. In other embodiments, the alternating magnetic fields result from the channel being positioned between first and second sets of magnets, in which first and second sets of magnets remain stationary and the channel is moved to alternate its proximity to the first and second sets of magnets, thereby producing the alternating magnetic fields.

Another aspect of the invention provides methods for detecting a target analyte in a sample including contacting a sample with magnetic particles including first moieties specific for a target analyte, thereby forming target/particle complexes in the sample, flowing the sample through a channel including second moieties attached to at least one surface of the channel, applying alternating magnetic fields to the flowing sample to result in target/particle complexes being brought into proximity of the surface of the channel to bind the second moieties and unbound particles remaining free in the sample, binding the target/particle complexes to the second moieties, washing away unbound particles and unbound analytes of the sample, eluting the target/particle complexes from the second moieties, and detecting the target/particle complexes.

BRIEF DESCRIPTION OF THE DRAWINGS

FIG. 2 panel A provides an exemplary process chart for implementation of methods of the invention for separation of bacteria from blood. Panel B provides an magnified view of a target/magnetic particle complex.

DETAILED DESCRIPTION

Figure 1:
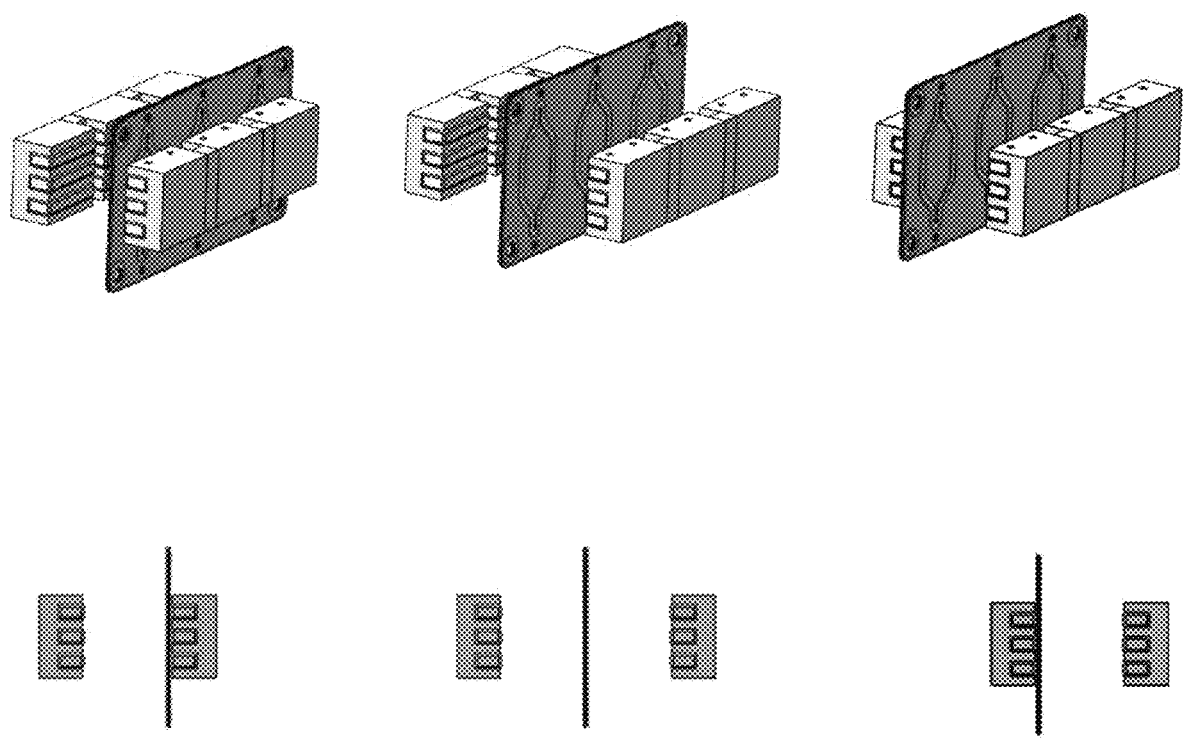
FIG. 1 provides one exemplary configuration of a flow cell and first and second sets of magnets for generating alternating magnetic fields.

The invention generally relates to using magnetic particles and alternating magnet fields to separate a target analyte from a sample. Methods of the invention involve contacting a sample with magnetic particles including first moieties specific for a target analyte, thereby forming target/particle complexes in the sample, flowing the sample through a channel including second moieties attached to at least one surface of the channel, applying alternating magnetic fields to the flowing sample to result in target/particle complexes being brought into proximity of the surface to bind the second moieties and unbound particles remaining free in the sample, binding the target/particle complexes to the second moieties, and washing away unbound particles and unbound analytes of the sample. Certain fundamental technologies and principles are associated with binding magnetic materials to target entities and subsequently separating by use of magnet fields and gradients. Such fundamental technologies and principles are known in the art and have been previously described, such as those described in Janeway (Immunobiology, 6$^{th}$ edition, Garland Science Publishing), the content of which is incorporated by reference herein in its entirety.

Methods of the invention involve collecting a sample having a target analyte in a container, such as a blood collection tube (e.g., Vacutainer) in the case of blood. In certain embodiments, a solution is added that prevents or reduces aggregation of endogenous aggregating factors, such as heparin in the case of blood.

Methods of the invention do not depend and are not limited by the type of sample. Any sample that includes a detectable target may be used with methods of the invention. The sample may be a biological sample (e.g., a human tissue or body fluid), a food sample, an agricultural sample, or an environmental sample (e.g., a water or soil sample).

Exemplary biological samples include human tissue or body fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, phlegm, saliva, sweat, amniotic fluid, mammary fluid, urine, sputum, and cerebrospinal fluid (CSF), such as lumbar or ventricular CSF. A sample may also be a fine needle aspirate. A sample also may be media containing cells or biological material. In particular embodiments, the sample is blood.

Exemplary agricultural samples include any plant material that is being interrogated by a method of the present invention. An agricultural sample includes, but is not limited to, seeds or plant tissue. Seeds include a single seed, a batch of seeds, a portion of a seed, or a seed scraping. Plant tissue includes, but is not limited to, any plant part such as leaf, flower, root, or petal. Plant tissue can also include a leaf punch.

Methods of the invention may be used to detect any target analyte. The target analyte refers to the substance in the sample that will be captured and isolated by methods of the invention. The target may be a bacteria, a fungi, a protein, a cell (such as a cancer cell, a white blood cell, a virally infected cell, or a fetal cell circulating in maternal circulation), a virus, a nucleic acid (e.g., DNA or RNA), a receptor, a ligand, a hormone, a drug, a chemical substance, or any molecule known in the art. In certain embodiments, the target is a pathogenic bacteria. In other embodiments, the target is a gram positive or gram negative bacteria. Exemplary bacterial species that may be captured and isolated by methods of the invention include *E. coli, Lysteria, Clostridium, Mycobacterium, Shigella, Borrelia, Campylobacter, Bacillus, Salmonella, Staphylococcus, Enterococcus, Pneumococcus, Streptococcus*, and a combination thereof.

The sample is then mixed with magnetic particles including a target-specific binding moiety to generate a mixture that is allowed to incubate such that the particles bind to a target in the sample, such as a bacteria in a blood sample. The mixture is allowed to incubate for a sufficient time to allow for the particles to bind to the target analyte. The process of binding the magnetic particles to the target analytes associates a magnetic moment with the target analytes, and thus allows the target analytes to be manipulated through forces generated by magnetic fields upon the attached magnetic moment.

In general, incubation time will depend on the desired degree of binding between the target analyte and the magnetic beads (e.g., the amount of moment that would be desirably attached to the target), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between 15° C. and 40° C.

Methods of the invention may be performed with any type of magnetic particle. Production of magnetic particles and particles for use with the invention are known in the art. See for example Giaever (U.S. Pat. No. 3,970,518), Senyi et al. (U.S. Pat. No. 4,230,685), Dodin et al. (U.S. Pat. No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic beads. In certain embodiments, the magnetic particle is an iron containing magnetic particle. In other embodiments, the magnetic particle includes iron oxide or iron platinum.

In certain embodiments, the magnetic particles include at least about 10% superparamagnetic beads by weight, at least about 20% superparamagnetic beads by weight, at least about 30% superparamagnetic beads by weight, at least about 40% superparamagnetic beads by weight, at least about 50% superparamagnetic beads by weight, at least about 60% superparamagnetic beads by weight, at least about 70% superparamagnetic beads by weight, at least about 80% superparamagnetic beads by weight, at least about 90% superparamagnetic beads by weight, at least about 95% superparamagnetic beads by weight, or at least about 99% superparamagnetic beads by weight. In a particular embodiment, the magnetic particles include at least about 70% superparamagnetic beads by weight.

In certain embodiments, the superparamagnetic beads are less than 100 nm in diameter. In other embodiments, the superparamagnetic beads are about 150 nm in diameter, are about 200 nm in diameter, are about 250 nm in diameter, are about 300 nm in diameter, are about 350 nm in diameter, are about 400 nm in diameter, are about 500 nm in diameter, or are about 1000 nm in diameter. In a particular embodiment, the superparamagnetic beads are from about 100 nm to about 250 nm in diameter.

In certain embodiments, the particles are beads (e.g., nanoparticles) that incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue bead aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the beads. It may also be advantageous to have the volumetric loading in a bead be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3 T.

The size of the nanometal containing bead may be optimized for a particular application, for example, maximizing moment loaded upon a target, maximizing the number of beads on a target with an acceptable detectability, maximizing desired force-induced motion, and/or maximizing the difference in attached moment between the labeled target and non-specifically bound targets or bead aggregates or individual beads. While maximizing is referenced by example above, other optimizations or alterations are contemplated, such as minimizing or otherwise desirably affecting conditions.

In an exemplary embodiment, a polymer bead containing 80 wt % $Fe_3O_4$ superparamagnetic particles, or for example, 90 wt % or higher superparamagnetic particles, is produced by encapsulating superparamagnetic particles with a polymer coating to produce a bead having a diameter of about 250 nm.

Magnetic particles for use with methods of the invention have a target-specific binding moiety that allows for the particles to specifically bind the target of interest in the sample. The target-specific moiety may be any molecule known in the art and will depend on the target to be captured and isolated. Exemplary target-specific binding moieties include, nucleic acids, proteins, ligands, antibodies, aptamers, and receptors.

In particular embodiments, the target-specific binding moiety is an antibody, such as an antibody that binds a particular bacteria. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such as target bacteria, effective to produce an immune response. An exemplary protocol is as follows. The animal is injected with 100 micrograms to 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Any antibody or fragment thereof having affinity and specific for the bacteria of interest is within the scope of the invention provided herein. Immunomagnetic beads against *Salmonella* are provided in Vermunt et al. (J. Appl. Bact. 72:112, 1992). Immunomagnetic beads against *Staphylococcus aureus* are provided in Johne et al. (J. Clin. Microbiol. 27:1631, 1989). Immunomagnetic beads against *Listeria* are provided in Skjerve et al. (Appl. Env. Microbiol. 56:3478, 1990). Immunomagnetic beads against *Escherichia coli* are provided in Lund et al. (J. Clin. Microbiol. 29:2259, 1991).

Methods for attaching the target-specific binding moiety to the magnetic particle are known in the art. Coating magnetic particles with antibodies is well known in the art, see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and Serology, Delmar, pp. 152-153, 2002). Such methodology can easily be modified by one of skill in the art to bind other types of target-specific binding moieties to the magnetic particles. Certain types of magnetic particles coated with a functional moiety are commercially available from Sigma-Aldrich (St. Louis, Mo.).

In certain embodiments, a buffer solution is added to the sample along with the magnetic beads. An exemplary buffer includes Tris(hydroximethyl)-aminomethane hydrochloride at a concentration of about 75 mM. It has been found that the buffer composition, mixing parameters (speed, type of mixing, such as rotation, shaking etc., and temperature) influence binding. It is important to maintain osmolality of the final solution (e.g., blood+buffer) to maintain high label efficiency. In certain embodiments, buffers used in methods of the invention are designed to prevent lysis of blood cells, facilitate efficient binding of targets with magnetic beads and to reduce formation of bead aggregates. It has been found that the buffer solution containing 300 mM NaCl, 75 mM Tris-HCl pH 8.0 and 0.1% Tween 20 meets these design goals.

Without be limited by any particular theory or mechanism if action, it is believed that sodium chloride is mainly responsible for maintaining osmolality of the solution and for the reduction of non-specific binding of magnetic bead through ionic interaction. Tris(hydroximethyl)-aminomethane hydrochloride is a well established buffer compound frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining blood cells intact.

An alternative approach to achieve high binding efficiency while reducing time required for the binding step is to use static mixer, or other mixing devices that provide efficient mixing of viscous samples at high flow rates, such as at or around 5 mL/min. In one embodiment, the sample is mixed with binding buffer in ratio of, or about, 1:1, using a mixing interface connector. The diluted sample then flows through a second mixing interface connector where it is mixed with target-specific nanoparticles. Additional mixing interface connectors providing mixing of sample and antigen-specific nanoparticles can be attached downstream to improve binding efficiency. The combined flow rate of the labeled sample is selected such that it is compatible with downstream processing. At this point in the process, the mixture includes target/magnetic particle complexes, unbound magnetic particles, and the remaining components of the mixture. Prior art techniques for isolating target/magnetic particle complexes involve applying a magnetic field to the mixture to capture the complexes on a surface. Components of the mixture that are not bound to magnetic particles will not be affected by the magnetic field and will remain free in the mixture.

The above described type of magnetic separation, produces efficient capture of a target analyte and the removal of a majority of the remaining components of a sample mixture. However, such a process produces a sample that contains a very high percent of magnetic particles that are not bound to target analytes because the magnetic particles are typically added in excess, as well as non-specific target entities. Non-specific target entities may be bound at a much lower efficiency, for example 1% of the surface area, while a target of interest might be loaded at 50% or nearly 100% of the available surface area or available antigenic cites. However, even 1% loading may be sufficient to impart force necessary for trapping in a magnetic gradient flow cell or sample chamber.

For example, in the case of immunomagnetic labeling of bacteria or fungi in a blood sample, the sample may include: labeled targets at a concentration of about 1/mL or a concentration less of about $10^6$/mL; background beads at a concentration of about $10^7$/ml to about $10^{10}$/ml; and non-specific targets at a concentration of about 10/ml to about $10^5$/ml.

The presence of magnetic particles that are not bound to target analytes and non-specific target entities on the surface that includes the target/magnetic particle complexes interferes with the ability to successfully detect the target of interest. The magnetic capture of the resulting mix, and close contact of magnetic particles with each other and labeled targets, result in the formation of aggregate that is hard to dispense and which might be resistant or inadequate for subsequent processing or analysis steps. Further, with addition of excess magnetic particles to the sample, a large number of particles may accumulate in the areas of high gradients, and thus a magnetically bound target analyte may likely be in the body of the accumulation of particles as opposed to the desired location adjacent the functionalized surface where specific binding may occur. Ignoring intra-bead forces (those forces associated with the magnetic field distribution of the individual beads and the forces these fields and associated gradients have on other beads), the beads may accumulate into large amorphous piles. Such intra-label forces do occur, and thus the aggregates of beads tend to exist in chains and long linear aggregates that are aligned with the 'field lines' of the magnetic trap pieces.

Methods of the invention address this problem by applying alternating magnetic fields to the sample as it flows through the channel. The frequency of the alternating magnetic field is selected such that the free magnetic nanoparticles cannot transverse the whole distance between top and bottom of the flow cell before the direction of the magnetic field is changed, causing nanoparticles to move in the opposite direction. Therefore, a majority of free nanoparticles will not come into close contact with active surfaces of the flow cell and will be washed away by liquid flow. Labeled target, due to higher magnetic moment, have higher velocity in the magnetic field and will reach a surface of the flow cell before change of the magnetic field, thus coming into close contact with the surface. This, in turn, will result in a specific binding event and result in a specific capture of the target analyte in the sample (such as a bacterium or other rare cell) to the surface coated with a second moiety. Components of the mixture that are not bound to magnetic particles will not be affected by the magnetic field and will remain free in the mixture.

The second target-specific moiety may be the same or different from the first target-specific moiety. The second moiety may be attached to the surface of the flow channel by methods described above relating to attaching first target-specific moieties to magnetic particles.

FIG. 1 provides one exemplary configuration of a flow cell and first and second sets of magnets for generating alternating magnetic fields. This figures shows that the flow cell is positioned between the first and second sets of magnetics. Either movement of the flow cell or movement of the magnets brings the flow cell closer to one set of magnets and further from the other set of magnets. Subsequent movement brings the flow cell within proximity of the other set of magnets. Such movements generate alternating magnetic fields within the channels of the flow cell that are felt by the unbound magnetic particles and the target/magnetic particle complexes.

In one embodiment, a flow cell may be about 15 mm wide and about 15 mm long, with a lead-in region and an lead-out section, and a height of about 0.5 mm (FIG. 1). A flow rate for such a cell may be about 100 µl/min, about 1 ml/min, about 10 ml/min, or from about 100 µl/min to about 10 ml/min or other ranges therein. A magnetic configuration may be an array of magnets, for example, an array of 7 bar magnets, or 5 bar magnets, or 3 bar magnets (FIG. 1). Magnets may be configured with alternating magnet poles facing one another, n-n, s-s, etc., with the pole face being normal to the array's rectangular face in this embodiment.

In a flowing system, successive encounters of unbound magnetic particles with a surface of a flow channel, without a resulting binding event, will allow the unbound magnetic particles to travel through the system and subsequently out of the cell. The cycling of the magnetic bar trap assemblies may be optimized based on the flow characteristics of the target(s) of interest. The expression of force on a magnetic moment and of terminal velocity for such target(s) is the following:

$$m \cdot (\text{del } B) = F \qquad \text{Equation 1}$$

$$v_t = -F/(6*p*n*r) \qquad \text{Equation 2}$$

where n is the viscosity, r is the bead diameter, F is the vector force, B is the vector field, and m is the vector moment of the bead.

A characteristic transit time across the height of the cell may be established. An efficient frequency of the alternating magnetic attractors, such that many surface interactions may be established prior to the exit from the flow cell, may be established. In certain embodiments, the transit time can be substantially different for the target of interest versus the unbound magnetic particles, or non-specific bound non-target. In such an embodiment, the target can be ensured to interact with surface a maximal amount of times, while the unbound magnetic particles or non-target can interact a minimal number of times, or not at all.

Because of the magnetizing characteristics of the particles, the unbound magnetic particles may form aggregates, which may be in the form of linear chains or clumps. This may be the case at high concentrations of beads. At all concentrations, the unbound magnetic particles may exhibit spatial poison statistics, and there is some probability that there will be a neighboring bead close enough to be captured by the forces associated with the magnetic field of the beads themselves. By using alternating magnetic fields, methods of the invention break up these linear aggregates, particularly when the spatial gradient field from the trap magnets is shifted faster than the unbound magnetic particles can move mutually to reorient to the new distribution of trap gradient. Particles organized in chains, with N—S axis co-aligned, may quickly be subjected to an external field that produces particle moments with the N—S poles shifted by 90°, and may produce very strong intra-particle repulsive forces. Transverse motion of the trap magnets serves this purpose in concert with, or as a discrete step in addition to, the alternation of the trapping magnets from one surface to the other.

In the optimization of the cycling timing of the trap magnets, the flow characteristics of the cell may be considered along with the spatial distribution of the gradient of the trap magnets. Flow characteristics may dictate the transport of the magnetic materials from entrance to exit of the cell, so that parabolic flow, plug flow, or any particular flow characteristic may be considered to facilitate obtaining desired deposition patterns and desired interactions with the surfaces of interest.

In certain embodiments, it may be desirable in various applications to maximize the encounters of the target/magnetic particle complexes with the functionalized surface of the channel, to minimize interference with the unbound magnetic particles, and/or to minimize adhesion of the unbound magnetic particles and non-specific materials to the surface. It may be advantageous to produce an array of pipes, or tubes, through which the flow of the sample materials may flow. By way of example, a 125 mm×15 mm×0.5 mm cell volume may be filled with tubes, longitudinally aligned with the cell flow direction, such that there is a great increase in the functionalized surface area and a limitation on the number of unbound magnetic particles that may interact and impede in the encounter of the target with the surface. Planar structures may be used for this purpose, in which the cell volume is constructed with multiple layers of smaller flow channels such that the surface area is increased and the number of unbound magnetic particles available to impede the target on its way to the surface is decreased. In this embodiment, the general approach of cycling the trap magnets is similar to that described above, but variables such as time constants, amplitudes and gradient field distributions, for example, are optimized for the particular situation. Similarly, in the case of transverse trap motion for the breaking-up of aggregates, the general approach is similar to that described above.

It may be desirable to shield the portion of the sample flow outside the trap cell from fringing magnetic field so that magnetic material does not have the opportunity to self-aggregate prior to entering the strong field and gradient zone of the trap. The magnetic materials and labeled target may also be trapped in flow tubes and other fluidic structures through magnetic forces in undesired areas. Shielding can be accomplished by the appropriate design of the trap magnets, for example, by managing the 'return path' of the field, and/or by using high permeability materials to capture and channel the field to minimize fringing field exposure.

It is possible to purify samples and fixate targets of interest and to then examine the target in situ on the surface, in any suitable manner known in the art, or the target can be removed from the surface by eluting off the surface through the use of an appropriate bonding chemistry that can be released such that the target can be analyzed in some subsequent process, for example, by use of a flowing system similar to a cytometer, or by collection of the individual targets for other analysis, such a NAT, PCR, etc, or some other post-processing and analysis as is enabled by the supply of target entity. In an exemplary case, the sample is analyzed using a flowing NMR detector.

Detection of bacteria of interest can be performed by use of nucleic acid probes following procedures which are known in the art. Suitable procedures for detection of bacteria using nucleic acid probes are described, for example, in Stackebrandt et al. (U.S. Pat. No. 5,089,386), King et al. (WO 90/08841), Foster et al. (WO 92/15883), and Cossart et al. (WO 89/06699), each of which is hereby incorporated by reference.

A suitable nucleic acid probe assay generally includes sample treatment and lysis, hybridization with selected probe(s), hybrid capture, and detection. Lysis of the bacteria is necessary to release the nucleic acid for the probes. The nucleic acid target molecules are released by treatment with any of a number of lysis agents, including alkali (such as NaOH), guanidine salts (such as guanidine isothiocyanate), enzymes (such as lysozyme, mutanolysin and proteinase K), and detergents. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization is includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of bacteria of interest can also be performed by use of PCR techniques. A suitable PCR technique is described, for example, in Verhoef et al. (WO 92/08805). Such protocols may be applied directly to the bacteria captured on the magnetic beads. The bacteria is combined with a lysis buffer and collected nucleic acid target molecules are then utilized as the template for the PCR reaction.

For detection of the selected bacteria by use of antibodies, isolated bacteria are contacted with antibodies specific to the bacteria of interest. As noted above, either polyclonal or monoclonal antibodies can be utilized, but in either case have affinity for the particular bacteria to be detected. These antibodies, will adhere/bind to material from the specific target bacteria. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies. For example, the second antibody may be conjugated to an enzyme, either alkaline phosphatase or to peroxidase. To detect the label, after the bacteria of interest is contacted with the second antibody and washed, the isolated component of the sample is immersed in a solution containing a chromogenic substrate for either alkaline phosphatase or peroxidase. A chromogenic substrate is a compound that can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include β-galactosidase, β-glucuronidase, α-glucosidase, β-glucosidase, α-mannosidase, galactose oxidase, glucose oxidase and hexokinase.

Detection of bacteria of interest using NMR may be accomplished as follows. In the use of NMR as a detection methodology, in which a sample is delivered to a detector coil centered in a magnet, the target of interest, such as a magnetically labeled bacterium, may be delivered by a fluid medium, such as a fluid substantially composed of water. In such a case, the magnetically labeled target may go from a region of very low magnetic field to a region of high magnetic field, for example, a field produced by an about 1 to about 2 Tesla magnet. In this manner, the sample may traverse a magnetic gradient, on the way into the magnet and on the way out of the magnet. As may be seen via equations 1 and 2 above, the target may experience a force pulling into the magnet in the direction of sample flow on the way into the magnet, and a force into the magnet in the opposite direction of flow on the way out of the magnet. The target may experience a retaining force trapping the target in the magnet if flow is not sufficient to overcome the gradient force.

Magnetic fields on a path into a magnet may be non-uniform in the transverse direction with respect to the flow into the magnet. As such, there may be a transverse force that pulls targets to the side of a container or a conduit that provides the sample flow into the magnet. Generally, the time it takes a target to reach the wall of a conduit is associated with the terminal velocity and is lower with increasing viscosity. The terminal velocity is associated with the drag force, which may be indicative of creep flow in certain cases. In general, it may be advantageous to have a high viscosity to provide a higher drag force such that a target will tend to be carried with the fluid flow through the magnet without being trapped in the magnet or against the conduit walls.

Newtonian fluids have a flow characteristic in a conduit, such as a round pipe, for example, that is parabolic, such that the flow velocity is zero at the wall, and maximal at the center, and having a parabolic characteristic with radius. The velocity decreases in a direction toward the walls, and it is easier to magnetically trap targets near the walls, either with transverse gradients force on the target toward the conduit wall, or in longitudinal gradients sufficient to prevent target flow in the pipe at any position. In order to provide favorable fluid drag force to keep the samples from being trapped in the conduit, it may be advantageous to have a plug flow condition, wherein the fluid velocity is substantially uniform as a function of radial position in the conduit.

When NMR detection is employed in connection with a flowing sample, the detection may be based on a perturbation of the NMR water signal caused by a magnetically labeled target (Sillerud et al., JMR (Journal of Magnetic Resonance), vol. 181, 2006). In such a case, the sample may be excited at time 0, and after some delay, such as about 50 ms or about 100 ms, an acceptable measurement (based on a detected NMR signal) may be produced. Alternatively, such a measurement may be produced immediately after excitation, with the detection continuing for some duration, such as about 50 ms or about 100 ms. It may be advantageous to detect the NMR signal for substantially longer time durations after the excitation.

By way of example, the detection of the NMR signal may continue for a period of about 2 seconds in order to record spectral information at high-resolution. In the case of parabolic or Newtonian flow, the perturbation excited at time 0 is typically smeared because the water around the perturbation source travels at different velocity, depending on radial position in the conduit. In addition, spectral information may be lost due to the smearing or mixing effects of the differential motion of the sample fluid during signal detection. When carrying out an NMR detection application involving a flowing fluid sample, it may be advantageous to provide plug-like sample flow to facilitate desirable NMR contrast and/or desirable NMR signal detection.

Differential motion within a flowing Newtonian fluid may have deleterious effects in certain situations, such as a situation in which spatially localized NMR detection is desired, as in magnetic resonance imaging. In one example, a magnetic object, such as a magnetically labeled bacterium, is flowed through the NMR detector and its presence and location are detected using MRI techniques. The detection may be possible due to the magnetic field of the magnetic object, since this field perturbs the magnetic field of the fluid in the vicinity of the magnetic object. The detection of the magnetic object is improved if the fluid near the object remains near the object. Under these conditions, the magnetic perturbation may be allowed to act longer on any given volume element of the fluid, and the volume elements of the fluid so affected will remain in close spatial proximity. Such a stronger, more localized magnetic perturbation will be more readily detected using NMR or MRI techniques.

If a Newtonian fluid is used to carry the magnetic objects through the detector, the velocity of the fluid volume elements will depend on radial position in the fluid conduit. In such a case, the fluid near a magnetic object will not remain near the magnetic object as the object flows through the detector. The effect of the magnetic perturbation of the object on the surrounding fluid may be smeared out in space, and the strength of the perturbation on any one fluid volume element may be reduced because that element does not stay within range of the perturbation. The weaker, less-well-localized perturbation in the sample fluid may be undetectable using NMR or MRI techniques.

Certain liquids, or mixtures of liquids, exhibit non-parabolic flow profiles in circular conduits. Such fluids may exhibit non-Newtonian flow profiles in other conduit shapes. The use of such a fluid may prove advantageous as the detection fluid in an application employing an NMR-based detection device. Any such advantageous effect may be attributable to high viscosity of the fluid, a plug-like flow profile associated with the fluid, and/or other characteristic (s) attributed to the fluid that facilitate detection. As an example, a shear-thinning fluid of high viscosity may exhibit a flow velocity profile that is substantially uniform across the central regions of the conduit cross-section. The velocity profile of such a fluid may transition to a zero or very low value near or at the walls of the conduit, and this transition region may be confined to a very thin layer near the wall.

Not all fluids, or all fluid mixtures, are compatible with the NMR detection methodology. In one example, a mixture of glycerol and water can provide high viscosity, but the NMR measurement is degraded because separate NMR signals are detected from the water and glycerol molecules making up the mixture. This can undermine the sensitivity of the NMR detector. In another example, the non-water component of the fluid mixture can be chosen to have no NMR signal, which may be achieved by using a perdeuterated fluid component, for example, or using a perfluorinated fluid component. This approach may suffer from the loss of signal intensity since a portion of the fluid in the detection coil does not produce a signal.

Another approach may be to use a secondary fluid component that constitutes only a small fraction of the total fluid mixture. Such a low-concentration secondary fluid component can produce an NMR signal that is of negligible intensity when compared to the signal from the main component of the fluid, which may be water. It may be advantageous to use a low-concentration secondary fluid component that does not produce an NMR signal in the detector. For example, a perfluorinated or perdeuterated secondary fluid component may be used. The fluid mixture used in the NMR detector may include one, two, or more than two secondary components in addition to the main fluid component. The fluid components employed may act in concert to produce the desired fluid flow characteristics, such as high-viscosity and/or plug flow. The fluid components may be useful for providing fluid characteristics that are advantageous for the performance of the NMR detector, for example by providing NMR relaxation times that allow faster operation or higher signal intensities.

A non-Newtonian fluid may provide additional advantages for the detection of objects by NMR or MRI techniques. As one example, the objects being detected may all have substantially the same velocity as they go through the detection coil. This characteristic velocity may allow simpler or more robust algorithms for the analysis of the detection data. As another example, the objects being detected may have fixed, known, and uniform velocity. This may prove advantageous in devices where the position of the detected object at later times is needed, such as in a device that has a sequestration chamber or secondary detection chamber down-stream from the NMR or MRI detection coil, for example.

In an exemplary embodiment, sample delivery into and out of a 1.7 T cylindrical magnet using a fluid delivery medium containing 0.1% to 0.5% Xanthan gum in water was successfully achieved. Such delivery is suitable to provide substantially plug-like flow, high viscosity, such as from about 10 cP to about 3000 cP, and good NMR contrast in relation to water. Xanthan gum acts as a non-Newtonian fluid, having characteristics of a non-Newtonian fluid that are well know in the art, and does not compromise NMR signal characteristics desirable for good detection in a desirable mode of operation.

FIG. 2 panel A provides an exemplary process chart for implementation of methods of the invention for separation of bacteria from blood. Sample is collected in sodium heparin tube by venipuncture, acceptable sample volume is 1-10 mL. Superparamagnetic particles having target-specific binding moieties are added to the sample, followed by incubation on a shaking incubator at 37° C. for 30-120 min.

Capture of the labeled targets allows for the removal of blood components and reduction of sample volume from 30 mL to 5 mL. The capture is performed by injecting the mixture of sample, unbound particles, and target/particle complexes into a channel that has target-specific antibodies coated on the surface. During the injection step, alternating magnetic fields are applied by a mechanical system that moves NdFeB permanent magnets (3 bars arranged in opposing orientation) on either side of the channel such that a magnet is present in close proximity only on one side of the channel. The frequency of the alternating magnetic field (1 Hz) was selected so that labeled targets would have sufficient time to reach one or both surfaces of the channel multiple times, while the majority of free beads would be prevented from reaching either surface of the channel.

After separation, target/particle complexes were eluted from the second moiety on the surface of the channel and flowed into an NMR machine for analysis. The detection method is based on a miniature NMR detector tuned to the magnetic resonance of water. When the sample is magnetically homogenous (no labeled targets), the NMR signal from water is clearly detectable and strong. The presence of magnetic material in the detector coil disturbs the magnetic field, resulting in reduction in water signal. One of the primary benefits of this detection method is that there is no magnetic background in biological samples which significantly reduces the requirements for stringency of sample processing. In addition, since the detected signal is generated by water, there is a built-in signal amplification which allows for the detection of a single labeled bacterium.

Using methods described herein, the following has been accomplished: binding of magnetic particles having bacteria-specific moieties to about 10,000 bacteria in about 5 ml of blood using about $5\times10^9$/ml of about 250 nm-diameter immunomagnetic label beads in an about 20 ml solution optimized for binding; separating the target from other components of the sample to produce a sample of about 5 ml targets and unbound magnetic particles; and removing virtually all unbound magnetic particles to enrich the sample into about 0.5 ml with about 61% of the starting bacteria.

Methods of the invention may also be combined with other separation and isolation protocols known in the art. Particularly, methods of the invention may be combined with methods shown in co-pending and co-owned U.S. patent application Ser. No. 12/850,203, filed Aug. 4, 2010, entitled Isolating A Target Analyte From A Body Fluid, the content of which is incorporated by reference herein in its entirety.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Sample

Blood samples from healthy volunteers were spiked with clinically relevant concentrations of bacteria (1-10 CFU/mL) including both laboratory strains and clinical isolates of the bacterial species most frequently found in bloodstream infections.

Example 2

Antibody Preparation

In order to generate polyclonal, pan-Gram-positive bacteria-specific IgG, a goat was immunized by first administering bacterial antigens suspended in complete Freund's adjuvant intra lymph node, followed by subcutaneous injection of bacterial antigens in incomplete Freund's adjuvant in 2 week intervals. The antigens were prepared for antibody production by growing bacteria to exponential phase ($OD_{600}$=0.4-0.8). Following harvest of the bacteria by centrifugation, the bacteria was inactivated using formalin fixation in 4% formaldehyde for 4 hr at 37° C. After 3 washes of bacteria with PBS (15 min wash, centrifugation for 20 min at 4000 rpm) the antigen concentration was measured using BCA assay and the antigen was used at 1 mg/mL for immunization. In order to generate Gram-positive bacteria-specific IgG, several bacterial species were used for inoculation: *Staphylococcus aureus, Staphylococcus epidermidis, Enterococcus faecium* and *Enterococcus fecalis.*

The immune serum was purified using affinity chromatography on a protein G sepharose column (GE Healthcare), and reactivity was determined using ELISA. Antibodies cross-reacting with Gram-negative bacteria and fungi were removed by absorption of purified IgG with formalin-fixed Gram-negative bacteria and fungi. The formalin-fixed organisms were prepared similar to as described above and mixed with IgG. After incubation for 1 hr at room temperature, the preparation was centrifuged to remove bacteria and absorption was repeated. Final antibody preparation was clarified by centrifugation and used for the preparation of antigen-specific magnetic beads.

Example 3

Preparation of Antigen-Specific Magnetic Beads

Superparamagnetic beads were synthesized by encapsulating iron oxide nanoparticles (5-15 nm diameter) in a latex core and labeling with goat IgG. Ferrofluid containing nanoparticles in organic solvent was precipitated with ethanol, nanoparticles were resuspended in aqueous solution of styrene and surfactant Hitenol BC-10, and emulsified using sonication. The mixture was allowed to equilibrate overnight with stirring and filtered through 1.2 and 0.45 μm filters to achieve uniform micelle size. Styrene, acrylic acid and divynilbenzene were added in carbonate buffer at pH 9.6. The polymerization was initiated in a mixture at 70° C. with the addition of $K_2S_2O_8$ and the reaction was allowed to complete overnight. The synthesized particles were washed 3 times with 0.1% SDS using magnetic capture, filtered through 1.2, 0.8, and 0.45 μm filters and used for antibody conjugation.

The production of beads resulted in a distribution of sizes that may be characterized by an average size and a standard deviation. In the case of labeling and extracting of bacteria from blood, the average size for optimal performance was found to be between 100 and 350 nm, for example between 200 nm to 250 nm.

The purified IgG were conjugated to prepared beads using standard chemistry. After conjugation, the beads were resuspended in 0.1% BSA which is used to block non-specific binding sites on the bead and to increase the stability of bead preparation.

Example 4

Attaching Target-Specific Antibodies to Surface of Flow Channel

Target-specific antibodies were attached to a surface of a flow channel using the following approach:

1. The surface was treated with 5M NaOH for 30 min at 37° C., followed by rinse with water and absorption of streptavidin, to coat the surface with streptavidin and provide means of attaching biotinylated antibodies;
2. Antibodies were biotinylated using des-thiobiotin, purified to remove excess biotin and attached to the surface through a specific binding to streptavidin.

The use of desthiobiotin allows for the elution of antibodies, and, therefore, bound target bacterium, using competitive elution with unmodified biotin. Other elution methods can be used, such as $Ni^{2+}$-chelating, GST-binding protein, etc.

Example 5

Separating Target from Remaining Components of the Sample

Target cells magnetically labeled using target-specific beads with the excess of free beads were injected into a channel that had target-specific antibodies coated on the surface. During the injection step, alternating magnetic field was applied by a mechanical system that moved NdFeB permanent magnets (3 bars arranged in opposing orientation) on either side of the channel such that a magnet was present in close proximity only on one side of the channel. The frequency of the alternating magnetic field (1 Hz) was selected so that labeled targets would have sufficient time to reach one or both surfaces of the channel multiple times, while the majority of free beads would be prevented from reaching either surface of the channel.

Example 6

Elution and Analysis of Target

Figure 3:
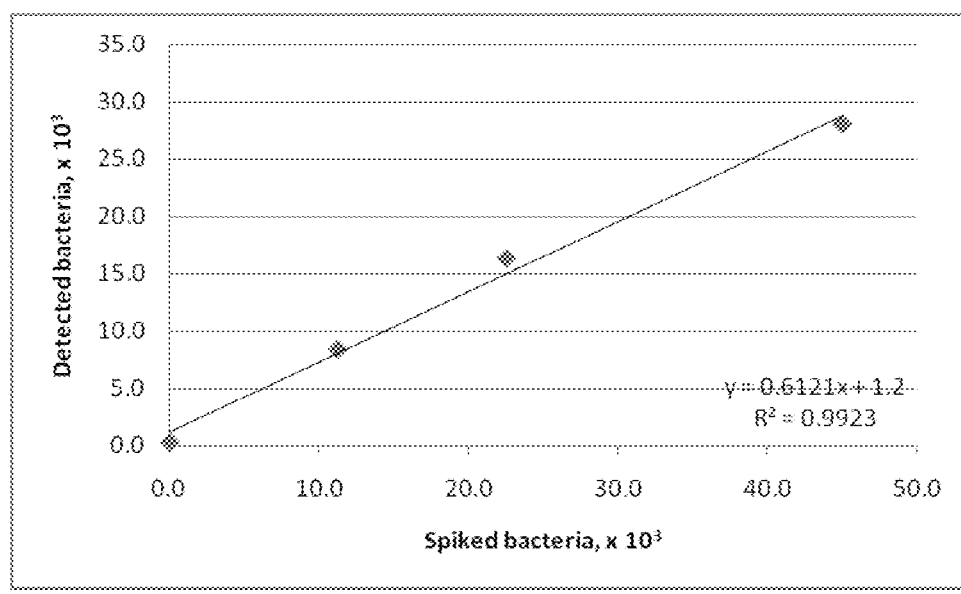
FIG. 3 is a graph showing recovery of bacteria from blood.

The bound bacteria were eluted with 35 mM biotin solution in B29, followed by magnetic capture and re-suspension in the detection buffer containing Xanthan gum. The concentration of bacteria in samples were analyzed in flow-through NMR detector. Results indicate that the number of detected bacteria was directly proportional to the number of bacteria spiked into blood (FIG. 3).

What is claimed is:
1. A method for detecting a target analyte in a sample, the method comprising:
   contacting a sample with magnetic particles comprising binding moieties specific for a target analyte;
   flowing the sample through a channel including second moieties specific to the target analyte attached to at least one surface of the channel while applying alternating magnetic fields to capture, on the at least one surface of the channel, magnetic particles that are bound to said target analyte;
   rinsing said channel to remove unbound components of said sample;
   eluting bound magnetic particle/second moiety/target analyte complexes from the at least one surface of the channel; and
   detecting the eluted magnetic particle/second moiety/target analyte complexes, wherein the magnetic particle/second moiety/target analyte complexes are not examined in situ on the at least one surface of the channel.
2. The method of claim 1, wherein detecting comprises the use of one or more processes selected from the group consisting of lysis, hybridization, cytometry, nucleic acid testing (NAT), polymerase chain reaction (PCR), and nuclear magnetic resonance (NMR).

3. The method of claim 1, wherein the target analyte is a bacterium.

4. The method of claim 1, wherein the sample is human tissue or body fluid.

5. The method of claim 4, wherein the body fluid is blood.

6. The method of claim 1, wherein the binding moieties are selected from the group consisting of antibodies, receptors, aptamers, proteins, and ligands.

7. The method of claim 1, wherein the binding moieties are antibodies.

\* \* \* \* \*